United States Patent
Rhee et al.

[11] Patent Number: 6,071,307
[45] Date of Patent: Jun. 6, 2000

[54] ENDOLUMINAL GRAFTS HAVING CONTINUOUSLY CURVILINEAR WIREFORMS

[75] Inventors: Richard Rhee, Diamond Bar; John McIntyre, Vista; Seik Oh, Laguna Hills, all of Calif.

[73] Assignee: Baxter International Inc., Deerfield, Ill.

[21] Appl. No.: 09/163,831

[22] Filed: Sep. 30, 1998

[51] Int. Cl.[7] .................................................. A61F 2/06
[52] U.S. Cl. ........................ 623/1.13; 623/1.2; 623/1.18
[58] Field of Search ............................. 623/11, 12, 1.13, 623/1.18, 1.2; 606/108, 191, 194, 195, 198

[56] References Cited

U.S. PATENT DOCUMENTS

| | | |
|---|---|---|
| 2,978,787 | 4/1961 | Liebig . |
| 5,064,435 | 11/1991 | Porter .......................................... 623/1 |
| 5,123,917 | 6/1992 | Lee . |
| 5,135,536 | 8/1992 | Hillstead . |
| 5,397,345 | 3/1995 | Lazarus ....................................... 623/1 |
| 5,443,497 | 8/1995 | Venbrux ...................................... 623/1 |
| 5,489,295 | 2/1996 | Piplani et al. ............................... 623/1 |
| 5,522,880 | 6/1996 | Barone et al. ............................... 623/1 |
| 5,527,354 | 6/1996 | Christiansen . |
| 5,554,181 | 9/1996 | Das ............................................... 623/1 |
| 5,562,726 | 10/1996 | Chuter .......................................... 623/1 |
| 5,562,728 | 10/1996 | Lazarus et al . ............................. 623/1 |
| 5,569,295 | 10/1996 | Lam . |
| 5,575,816 | 11/1996 | Rudnick et al. ............................. 623/1 |
| 5,575,817 | 11/1996 | Martin ......................................... 623/1 |
| 5,591,197 | 1/1997 | Orth et al. . |
| 5,591,230 | 1/1997 | Horn et al. .................................. 623/1 |
| 5,603,721 | 2/1997 | Lau et al. . |
| 5,609,605 | 3/1997 | Marshall et al. ......................... 606/191 |
| 5,630,829 | 5/1997 | Lauterjung . |
| 5,676,696 | 10/1997 | Marcade ...................................... 623/1 |
| 5,676,697 | 10/1997 | McDonald .................................. 623/1 |
| 5,683,449 | 11/1997 | Marcade ...................................... 623/1 |
| 5,683,453 | 11/1997 | Palmaz ......................................... 623/1 |
| 5,776,161 | 7/1998 | Globerman .................................. 623/1 |
| 5,782,904 | 7/1998 | White et al. ................................. 623/1 |
| 5,797,949 | 8/1998 | Parodi ....................................... 606/194 |
| 5,824,039 | 10/1998 | Piplani et al. ............................... 623/1 |
| 5,824,055 | 10/1998 | Spiridigliozzi et al. ..................... 623/1 |
| 5,871,536 | 2/1999 | Lazarus ....................................... 623/1 |
| 5,925,061 | 7/1999 | Ogi et al. ..................................... 623/1 |
| 5,928,280 | 7/1999 | Hansen et al. .............................. 623/1 |
| 5,931,866 | 8/1999 | Frantzen ...................................... 623/1 |

FOREIGN PATENT DOCUMENTS

| | | |
|---|---|---|
| 0657147 | 6/1995 | European Pat. Off. . |
| 0662307 | 7/1995 | European Pat. Off. . |
| 0686379 | 12/1995 | European Pat. Off. . |
| 0701800 | 3/1996 | European Pat. Off. . |
| 0712614 | 5/1996 | European Pat. Off. . |

*Primary Examiner*—Michael J. Milano
*Assistant Examiner*—Tram A. Nguyen
*Attorney, Agent, or Firm*—Baxter Hlthcare; Peter Jon Gluck, Esq.; Guy Cumberbatch, Esq.

[57] ABSTRACT

An endoluminal grafts is provided which is constructed to be radially collapsed and/or radially compressed to a small diameter. The graft has wireforms which generally comprise a wire deformed into generally annular configuration and consisting of a plurality of curvilinear wave forms. The wave forms have a plurality of first apices in linear alignment with each other, a plurality of second apices in linear alignment with each other, and a plurality of curvilinear segments traversing back and forth between said first and second apices. The graft is i) initially disposable in a radially compact configuration of a first diameter and ii) subsequently expandable to a radially expanded configuration of a second diameter, said second diameter being larger than said first diameter. When in its radially compact configuration, the adjacent curvilinear segments of the wireforms will nest or seat in abutting contact with one another, thereby minimizing the diameter of the graft while in its radially compact configuration.

26 Claims, 4 Drawing Sheets

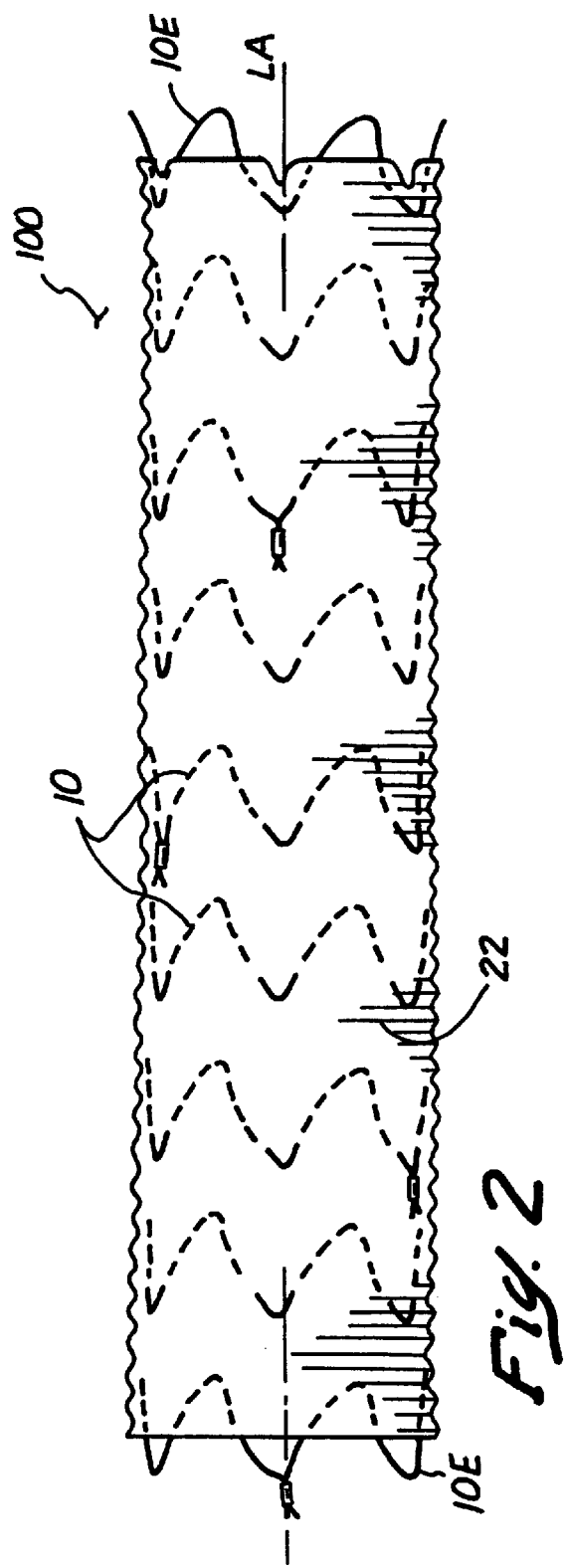
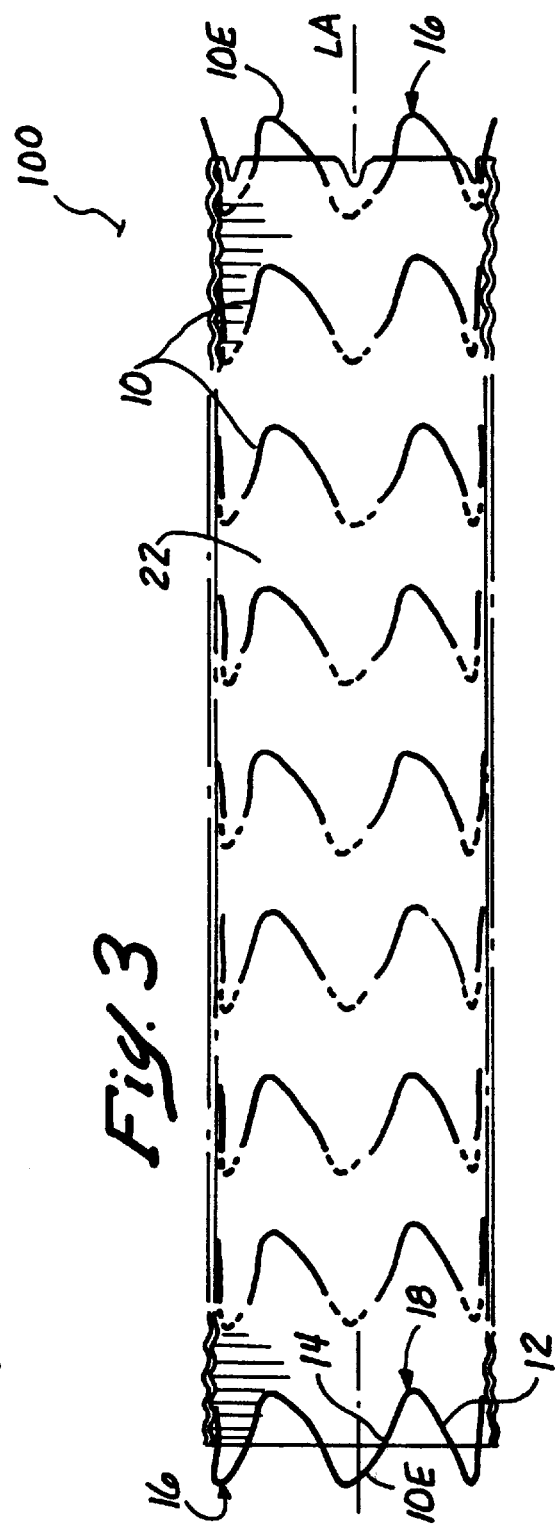

ENDOLUMINAL GRAFTS HAVING CONTINUOUSLY CURVILINEAR WIREFORMS

FIELD OF THE INVENTION

The present invention relates generally to medical devices, and more particularly to a radially expandable, endoluminal grafts which may be implanted within the lumen of a luminal anatomical structure.

BACKGROUND OF THE INVENTION

In modern medical practice, it is common to implant radially expandable grafts and similar devices within body lumens (e.g., blood vessels, esophagus, common bile duct, ureter, urethra, fallopian tube, etc.)

In general intraluminal grafts and their respective support and/or attachment means fall into two major categories, self-expanding and pressure expandable. Self-expanding intraluminal grafts, are formed of resilient or shape-memory material such as spring steel or Nitinol™. Self-expanding material is capable of being formed in a configuration from which it may be compressed to a radially compact diameter for placement within a damaged vessel. At the time of use, the memory feature of these materials causes them to self-expand from the radially compact diameter to the expanded operative diameter.

Pressure-expandable intraluminal grafts are formed of plastically deformable material such as stainless steel that is initially formed in its radially compact diameter. This type of material does not have memory, and will remain in the radially compact diameter until manually expanded. Typically, outwardly directed pressure is exerted upon the graft through use of a balloon so as to cause radial expansion and resultant plastic deformation of the material to its operative diameter.

The prior art has included numerous endovascular grafts of varying design. In general, these endovascular grafts typically comprise: a tube of pliable material (e.g., expanded polytetrafluoroethylene (ePTFE) or woven polyester) in combination with a graft anchoring component (e.g., a wireform, a frame, a series of wire rings, hooks, barbs, clips, staples, etc.) which operates to hold the tubular graft in its intended position within the blood vessel. Most commonly, the graft anchoring component is formed of a radially expandable frame (e.g., one or more radially-expandable wireforms of the type described hereabove) which is either a) incorporated into the body of the tubular graft or b) formed separately from the graft and positioned within the graft lumen, such frame being expandable to exert outwardly directed radial pressure against the surrounding blood vessel wall—thereby frictionally holding the graft in place. In operation, endovascular grafts which incorporate radially expandable graft anchoring devices are initially disposed in a radially collapsed configuration which is sufficiently compact to allow the graft to be transluminally advanced through the vasculature until it reaches the intended site of implantation. Thereafter, the graft (and the accompanying graft anchoring device) expands to a radially expanded configuration which is large enough to exert the desired outwardly-directed pressure against the blood vessel wall.

In some embodiments, hooks, barbs, or other projections formed on the graft anchoring device, will insert into the wall of the blood vessel to ensure that the graft will be firmly held in its desired position, without slipping or migrating after implantation. Like the above-described wireforms, the radially expandable anchoring devices (e.g., frames or wireforms) of endoluminal grafts are generally classifiable as either a.) self-expanding or b) pressure-expandable. Graft anchoring devices of the self-expanding type are usually formed of a resilient material (e.g., spring metal) or shape memory alloy which automatically expands from a radially collapsed configuration to a radially expanded configuration, when relieved of surrounding constraint (e.g., a surrounding tubular sheath or catheter wall). On the other hand, those of the pressure-expandable variety are typically formed of malleable wire or other plastically deformable material which will deform to a radially expanded configuration in response to the exertion of outwardly directed pressure thereagainst—as by inflation of a balloon or actuation of another pressure-exerting apparatus which has been positioned within the graft anchoring device.

In order to facilitate the transluminal, catheter based implantation of endoluminal grafts, it is typically desirable to minimize the diameter of the graft while in its radially compact configuration, thereby minimizing the required diameter of the delivery catheter used for delivery and implantation of the graft. In general, the smaller the diameter of the delivery catheter the smaller the size of the percutaneous puncture tract required for introduction of the catheter. Moreover, in many applications, it is necessary for the catheter to fit through relatively small body lumens and, thus, the diameter of the catheter must not exceed that of the body lumen(s) through which it must pass.

Moreover, the act of radially compressing or collapsing a graft can result in the introduction of stress within the wireform. In some cases, the introduction of such stresses can adversely affect the performance of the graft following implantation.

In view of these considerations, there exists a need in the art for the development of new wireforms which i) are capable of being radially compressed or radially collapsed to a small diameter so as to be useable in conjunction with relatively small diameter delivery catheters, and ii) will undergo minimal stress inducement during the radial compression/compaction process so as to minimize any deleterious effects that induced or residual stress may have on the subsequent performance and useful life of the graft.

SUMMARY OF THE INVENTION

The present invention provides new grafts which are constructed to be radially collapsed and/or radially compressed to a small diameter. The wireforms of the present invention generally comprise a wire deformed into generally annular configuration and consisting of a plurality of curvilinear wave forms. The wave forms have a plurality of first apices in linear alignment with each other, a plurality of second apices in linear alignment with each other, and a plurality of curvilinear segments traversing back and forth between said first and second apices. This graft is i) initially disposable in a radially compact configuration of a first diameter and ii) subsequently expandable to a radially expanded configuration of a second diameter, said second diameter being larger than said first diameter. When in its radially compact configuration, the adjacent curvilinear segments of the wireforms will nest or seat in abutting contact with one another, thereby minimizing the diameter of the graft while in its radially compact configuration.

Further in accordance with the invention, there are provided endoluminal or endovascular grafts which comprise one or more wireforms of the foregoing character, affixed to a pliable tubular graft such that the wireforms will act as a radially expandable graft anchoring device to frictionally anchor and hold the graft at its desired position within the lumen of a blood vessel or other anatomical conduit.

Still further objects and advantages of the invention will be apparent to those skilled in the art upon reading and understanding the following detailed description of exemplary embodiments shown in the accompanying drawings.

BRIEF DESCRIPTION OF THE DRAWINGS

FIG. 2 is a side elevational view of an endoluminal graft of the present invention, showing the locations and configurations of the continuously curvilinear members mounted within the graft.

FIG. 3 is a longitudinal sectional view of the endoluminal graft of FIG. 2.

DETAILED DESCRIPTION OF PREFERRED EMBODIMENTS

FIGS. 1–6 show an endoluminal graft 100 of the present invention, which comprises a pliable tube 22 having a plurality of radially expandable ring members 10 affixed thereto. The radially expandable ring members 10 combine to form a graft anchoring system (i.e., a series of individual ring members 10) which, when radially expanded within the lumen of an anatomical conduit, will exert outward force against the surrounding wall of the anatomical conduit to hold the endoluminal graft 100 in a substantially fixed position therewithin.

Figure 4:
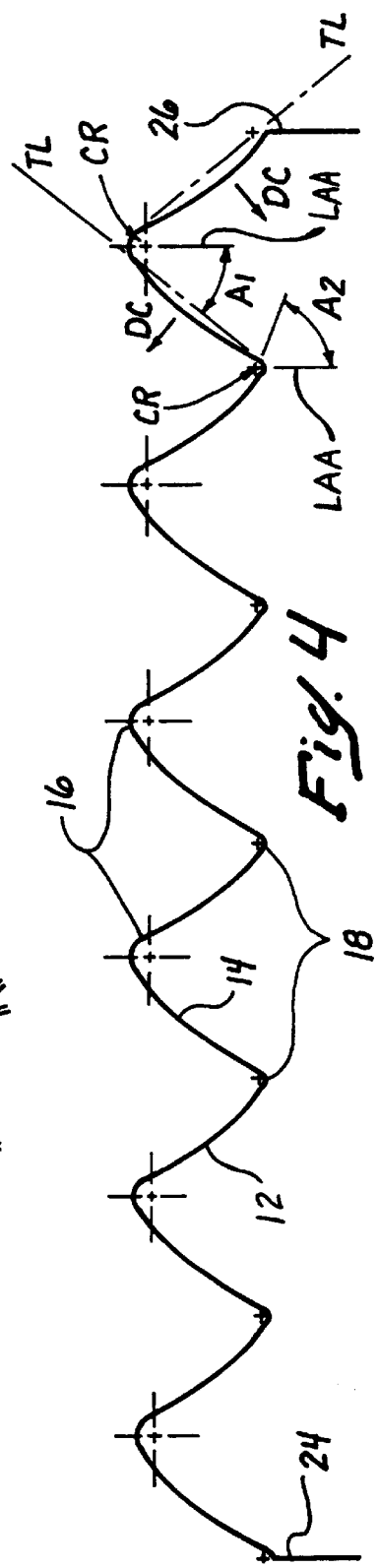
FIG. 4 is a plan view of one (1) of the continuously curvilinear members of the endoluminal graft of FIG. 2.

A. Structure of the Ring Members:

Referring particularly to the showing of a flattened ring member 10 provided as FIG. 4, each ring member 10 comprises a series of curvilinear segments 12, 14 which extend, in zig-zag fashion, between apices 16, 18. A tangent line TL is projectable in relation to each curvilinear segment 12 or 14, and the direction in which the curvilinear segment 12, 14 diverges from its tangent line TL is herein referred to as its direction of curvature DC. A center of radius CR is definable within each apex 16, 18, and a longitudinal apical axis LAA may be projected through each center of radius CR, as shown. An internal angle $A_1$ of preferably about 37.5 degrees, and an external angle $A_2$ of preferably about 70 degrees, are defined between each longitudinal apical axis LAA and the adjacent tangent lines TL which relate to the curvilinear segments 12, 14 on either side of that longitudinal apical axis LAA. Each curvilinear segment 12, 14 connects to the curvilinear first and second apices 16, 18 at points of tangency. The internal angle $A_1$ is the angle that each of the tangent lines TL make with respect to the adjacent longitudinal apical axes LAA, and the external angle $A_2$ is the angle with respect to the corresponding LAA along the respective curvilinear first and second apices 16, 18 at which the points of tangency are located. The values of the internal angle $A_1$ and the external angle $A_2$, of course, are not limited to the described preferred embodiments and it will be understood by those skilled in the art that other values also within the scope of the present invention.

Figure 1:
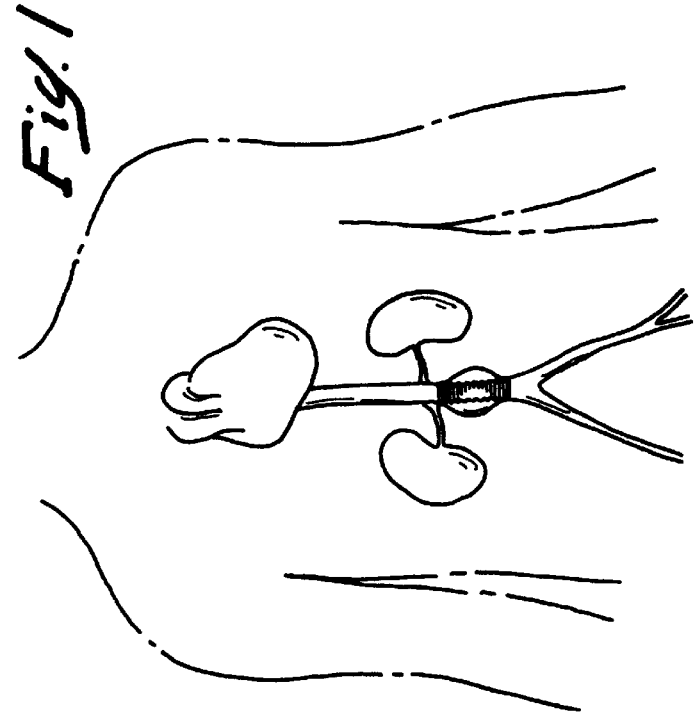
FIG. 1 is a schematic view of a human body having an endoluminal graft of the present invention implanted within the abdominal aorta, to treat an aortic aneurysm.
Figure 9:
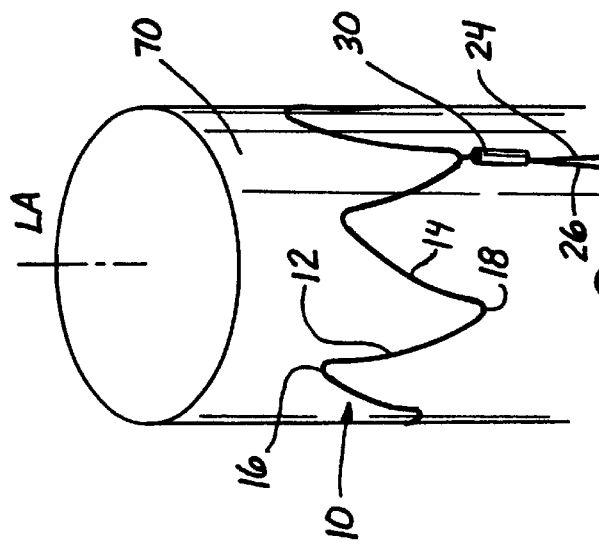
FIG. 9 is a perspective view of one end of a cylindrical mandrel being used to perform a second step in the formation of a continuously curvilinear member of the present invention.

As shown in FIG. 9, the individual curvilinear segments 12, 14 of each ring member 10 are affixed to or continuous with one another, and are formed about a longitudinal axis LA to form a ring. Depending on the physical properties of the material of which the ring members 10 are formed, the ring members 10 may be either pressure expandable or self expanding.

Ring members 10 of the pressure-expandable (i.e., "passive expandable") variety may be formed of plastically deformable material (e.g., stainless steel or Elgiloy™) which is compressible and plastically deformable to a first (radially compact) diameter and remains stable in such first diameter until such time as outwardly directed pressure is applied thereto (e.g., by inflation of a balloon positioned within the interior of the radially collapsed ring member) to cause radial expansion and resultant plastic deformation to a second (operative) diameter.

Ring members 10 of the self-expanding variety may be formed of resilient or shape memory material (e.g., spring steel or Nitinol™) which is capable of self-expanding from its first (radially compact) diameter to its second (operative) diameter without the exertion of outwardly directed force thereagainst.

B. Use of the Ring Members as Stents:

Each ring member 10 may thus be used individually as a radially expandable intraluminal stent, whereby the alternating zig-zag configuration of the curvilinear members 12, 14 will form a support scaffold which will prevent surrounding tissue from invading the interior thereof. In this manner the ring members 10 comprise stents which may be implanted in blood vessels or other luminal anatomical structures to maintain patency thereof.

When it is desired to use a ring member 10 as a stent, the ring member 10 may be initially mounted upon or within a delivery catheter for introduction into, and implantation within, the desired anatomical structure. In pressure-expandable embodiments, by way of example and not limitation this may be accomplished by mounting the ring member 10 in a radially compressed state upon a balloon catheter, while the balloon of the catheter is deflated. Thereafter, the catheter is inserted and advanced through the body lumens (e.g., blood vessels) until the ring member 10 is positioned at the desired site of implantation. Thereafter, the balloon of the catheter is inflated causing the ring member 10 to radially expand until it engages the surrounding wall of the anatomical structure (e.g., blood vessel). Thereafter, the balloon is deflated and the catheter is removed, leaving the ring member implanted as a stent within the luminal anatomical structure (e.g., blood vessel). Self-expanding embodiments and any known methods of their implantation are also within the scope of the present invention.

C. Endoluminal Grafts Incorporating the Ring Members:

FIGS. 1–3 and 5–6 show an endoluminal graft 100 wherein a plurality of the ring members 10 of the present invention are used to form a graft anchoring system. The endoluminal graft 100 comprises a pliable tube graft 22 having a series of the ring members 10 affixed to the tube graft 22 at spaced-apart locations or intervals, as shown. As illustrated particularly in FIGS. 2 and 3, the apices 16, 18 of the ring members 10 are preferably in direct alignment with one another and the curvilinear segments 12, 14 are also substantially aligned and are of the substantially the same direction of curvature DC. In this manner, when the endoluminal graft 100 is collapsed (e.g., compressed or allowed to retract) to its radially collapsed configuration, the curvilinear segments 12, 14 of each ring member 10 will become nested within each other so as to allow the diameter of the endoluminal graft 100 to be reduced substantially—to form a relatively low profile configuration.

It will be appreciated that the pliable tube graft 22 may be formed of any suitable material, including but not limited to woven polyester, expanded polytetrafluoroethylene (ePTFE), etc. In the exemplary embodiment shown in FIGS. 1–3 and 5–6, the tube graft 22 is formed of woven polyester and the individual ring members 10 are threaded through slits 40 formed in the tube graft 22 such that the ring members 10 will be held in substantially fixed positions within the tube graft 22. The ring members 10 may be unconnected to one another other than by way of their common attachment to the pliable tube graft. On the other hand, if desired, they may be attached to one another other than by way of their common attachment to the pliable tube graft. This mode of construction of the endoluminal graft 100 is generally in accordance with that described in U.S. Pat. No. 5,782,904 to White et al., which is incorporated herein by reference. Of course, other types of attachments of the ring members 10 to the tube graft 22 are within the scope of the present invention.

Figure 5:
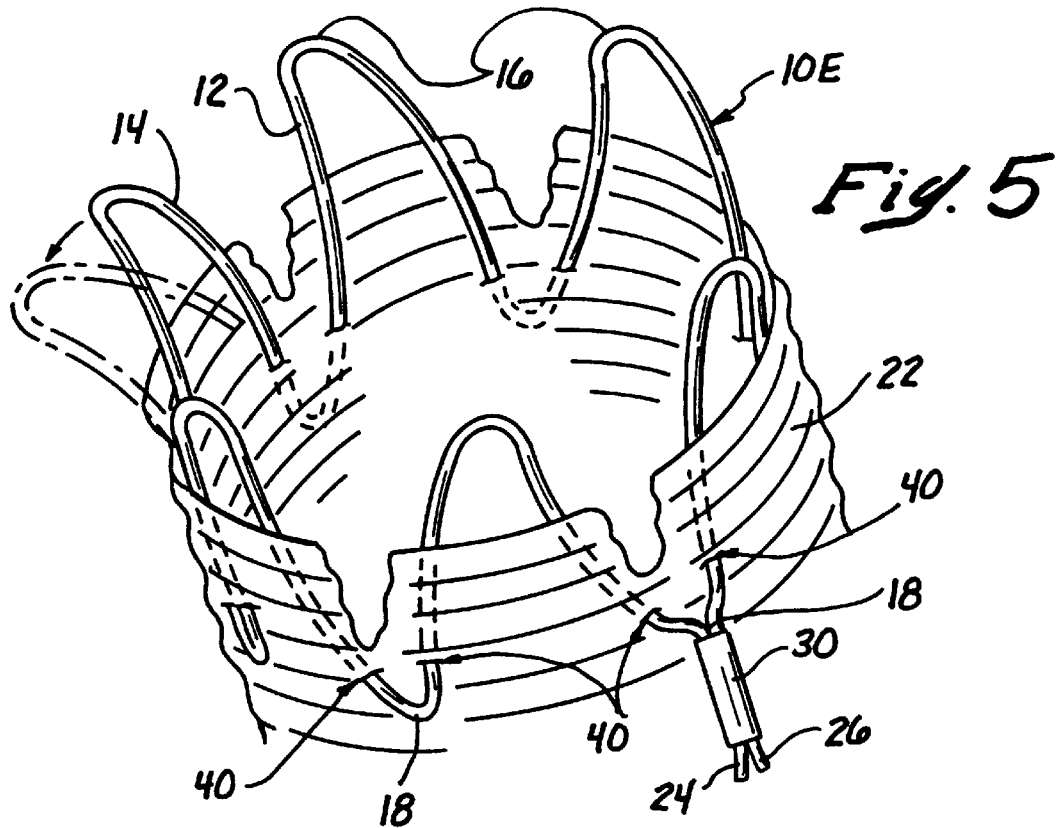
FIG. 5 is perspective view of one end of the endoluminal graft of FIG. 2.
Figure 6:
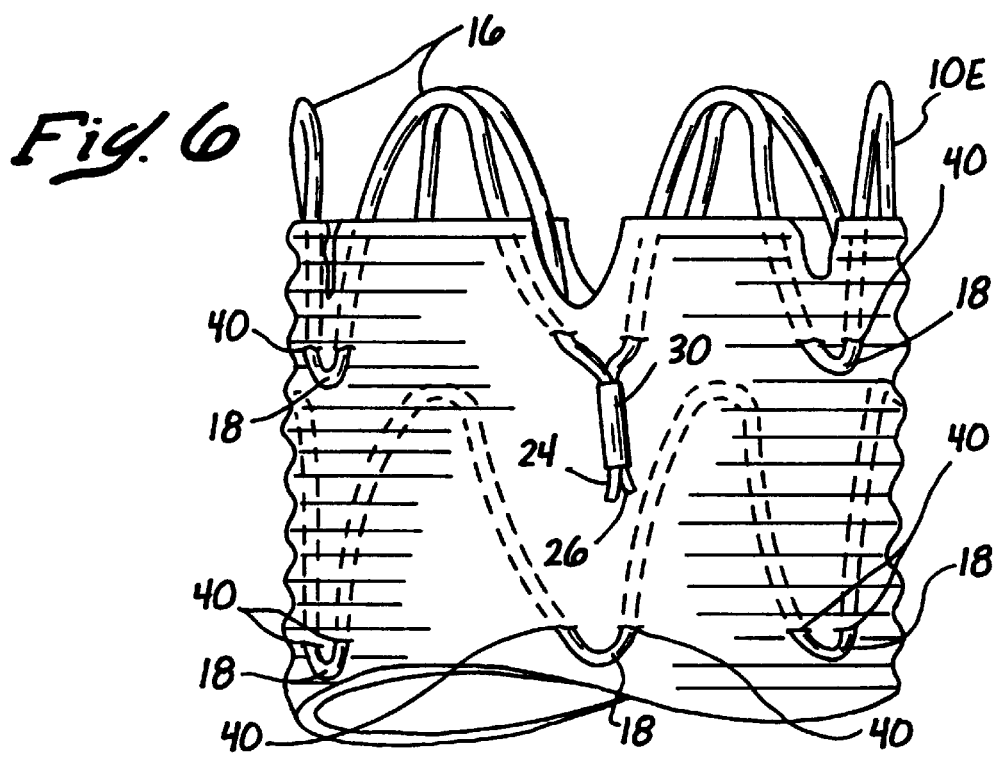
FIG. 6 is a side elevational view of the endoluminal graft of FIG. 2.

In some applications, it may be desirable to position the terminal ring members 10$_E$ located at either end of the endoluminal graft 100 such that their first apices 16 protrude beyond the end of the tube graft 22, as particularly shown in FIGS. 5 and 6. Additionally, the protruding portions of the terminal ring members 10$_E$ may be bent outwardly in the manner indicated by phantom lines on FIG. 5, to enhance the frictional engagement of those terminal ring members 10$_E$ with the tissue of the surrounding wall of the anatomical structure. The protruding portions 10$_E$ are described in great details in U.S. Pat. No. 5,782,904 to White et al., which is incorporated herein by reference.

Figure 7:
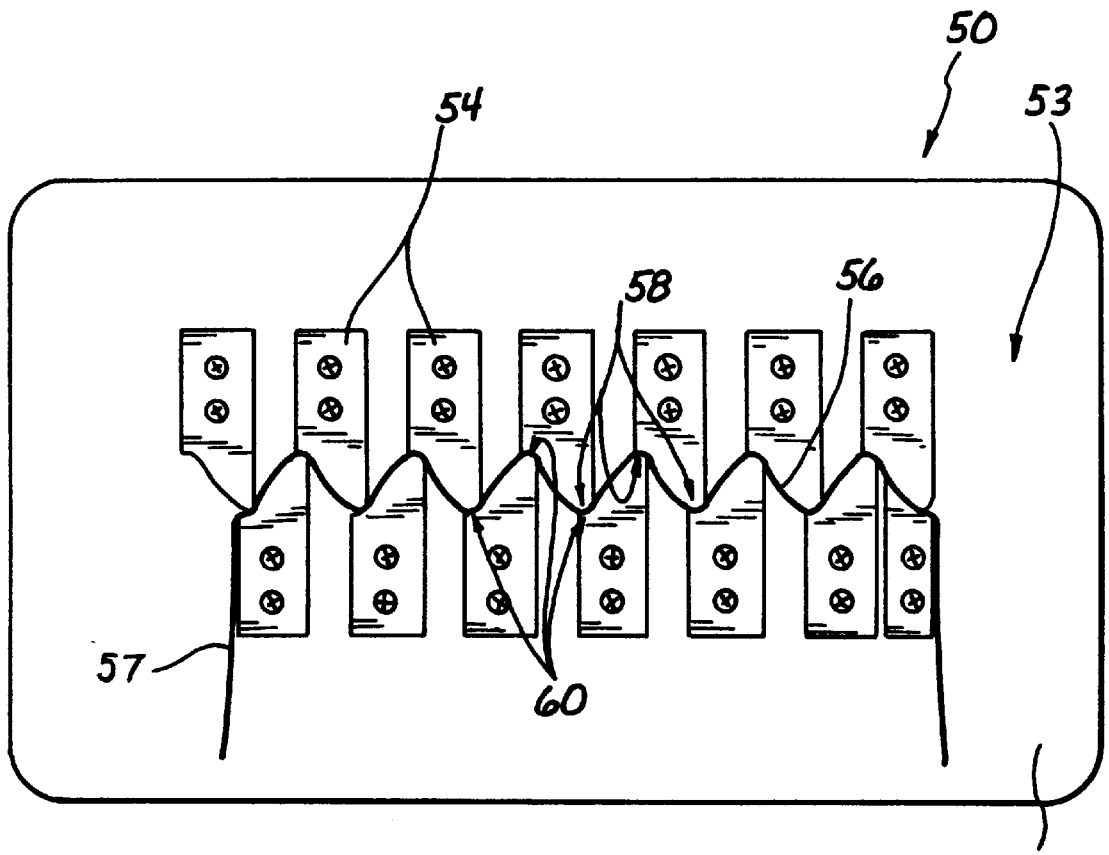
FIG. 7 is a plan view of a fixture apparatus of the present invention being used to perform a first step in the formation of a continuously curvilinear member of the present invention.
Figure 8:
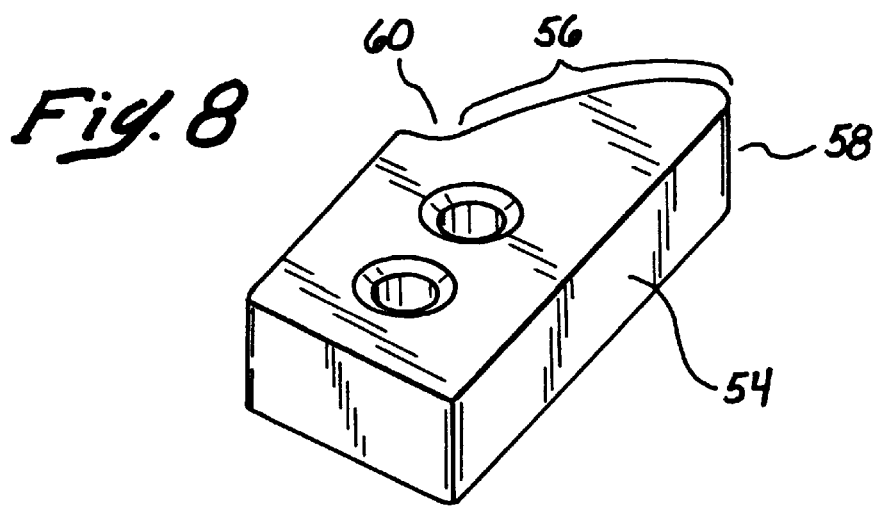
FIG. 8 is a perspective view of a wireform guide member which is a component of the fixture apparatus of FIG. 7.

D. Apparatus and Method for Manufacturing the Ring Members:

FIGS. 7–9 show a fixture apparatus and method for forming a ring member 10 of the present invention from a single piece of wire 57. As shown specifically in FIGS. 7 & 8, the preferred fixture apparatus 50 comprises a backboard 52 which has a flat surface 53 and a plurality of wire-forming block members 54 mounted on such flat surface 53. Each block member 54 has a curved wire-abutting edge 56, an apical tip 58, and an apical trough 60. The block members 54 are mounted on the back board 52 such that the apical tip 58 of one block member 54 is in close-spaced juxtaposition with the apical trough 60 of the next block member 54, as shown. The distance between the apical tip 58 of one block member 54 and the apical trough 60 of the next block member 54 is approximately equal to the diameter of the wire 57.

A preferred wire 57 for use in forming the ring members 10 is an alloy wire available commercially as Elgiloy™ wire from Elgiloy, Elgin, Ill. Other wires which may be useable include stainless steel wire and other implantable metals.

The wire 57 is threaded between the block members 54 such that the wire 57 abuts against the curved surfaces 56 to form the curvilinear segments 12, 14, and is interposed between the adjacent apical tips 58 and apical troughs 60 to form the first and second apices 16, 18. In this manner, the wire 57 assumes the desired flattened wireform configuration shown in FIG. 4.

As shown specifically in FIG. 9, after the wire 57 has been formed upon the fixture apparatus 50, it is removed from the fixture apparatus 52 and is the formed about a cylindrical mandrel 70 to impart the desired ring configuration. When formed about the mandrel 70, the free ends tails 24, 26 of the wire 57 are in side by side juxtaposition. Such free end tails 24, 26 are then twined about one another to overlap and a sleeve member 30 is crimped thereabout to firmly connect the twined portions of the free end tails 24, 26 immediately adjacent the associated second apex 18. Thereafter any portions of the free end tails 24, 26 which protrude from the crimped sleeve member 30 may be cut away, and the finished ring member 10 is removed from the mandrel 70. Alternatively, the plurality of curvilinear segments of each ring member may be initially formed as separate, curvilinear segments and subsequently connected to one another to form that ring member.

It is to be appreciated that the invention has been described herein with reference to certain exemplary embodiments only, and no effort has been made to exhaustively describe each and every possible embodiment of the invention. Indeed, as those skilled in the art will appreciate, various additions, deletions, modifications and/or alterations may be made to the above described embodiments without departing from the intended spirit and scope of the invention. It is intended that all such additions, deletions, alterations and modifications be included within the scope of the following claims.

What is claimed is:

1. An intraluminal graft, comprising:
   a biocompatible pliable tube, and
   a support scaffold connected to the tube including at least one annular wireform, each wireform defining a central axis and including:
      a wire shaped with a plurality of curvilinear waveforms, the waveforms having a plurality of first co-planar apices and a plurality of second co-planar apices, the first and second apices alternating and extending in opposite directions, and a plurality of curvilinear segments extending between and connecting the alternating first and second apices, the curvilinear segments each having a direction of curvature in the same rotational orientation about the central axis as an adjacent curvilinear segment.

2. The graft of claim 1, wherein the wireform is formed at least partially of resilient material and biased to said radially expanded configuration such that said wireform will self-expand to said radially expanded configuration when at body temperature and unconstrained.

3. The graft of claim 1, wherein said wireform is at least partially formed of malleable material which is initially formed to said radially compact configuration, and is plastically deformable to said radially expanded configuration.

4. The graft of claim 1, wherein the first and second apices are curvilinear and have radii of curvature and a corresponding center of radius.

5. The graft of claim 4, wherein each curvilinear segment connects to the adjacent first and second apices at points of tangency along the respective radii of curvature of the first and second apices.

6. The graft of claim 5, wherein each of a plurality of longitudinal apical axes extends in parallel to the central axis and through the center of radius of the first and second apices, and wherein a tangent line drawn between the points of tangency at the opposite ends of any one curvilinear segment defines an internal angle with respect to the adjacent longitudinal apical axes of about 37.5°.

7. The graft of claim 6, wherein the points of tangency at the opposite ends of any one curvilinear segment are located along the respective curvilinear first and second apices at an external angle of about 70° with respect to the corresponding longitudinal apical axes.

8. The graft of claim 1, wherein the support scaffold includes a plurality of the wireforms each spaced apart.

9. The graft of claim 8, wherein the graft is straight and the central axes of the plurality of wireforms are co-linear.

10. The graft of claim 8, wherein the first apices of the plurality of wireforms are aligned.

11. The graft of claim 1, wherein the wireform of the support scaffold is located substantially within the pliable tube.

12. The graft of claim 11, wherein the wireform is threaded through apertures provided in the pliable tube.

13. A wireform for medical stents or grafts, comprising:
a ring-shaped wireform defining a central axis and including a wire shaped with a plurality of curvilinear waveforms, the waveforms having a plurality of first co-planar apices and a plurality of second co-planar apices, the first and second apices alternating and extending in opposite directions, and a plurality of curvilinear segments extending between and connecting the alternating first and second apices, the curvilinear segments each having a direction of curvature in the same rotational orientation about the central axis as an adjacent curvilinear segment.

14. The wireform of claim 13, wherein the first and second apices are curvilinear and have radii of curvature and a corresponding center of radius.

15. The wireform of claim 14, wherein each curvilinear segment connects to the adjacent first and second apices at points of tangency along the respective radii of curvature of the first and second apices.

16. The wireform of claim 15, wherein each of a plurality of longitudinal apical axes extends in parallel to the central axis and through the center of radius of the first and second apices, and wherein a tangent line drawn between the points of tangency at the opposite ends of any one curvilinear segment defines an internal angle with respect to the adjacent longitudinal apical axes of about 37.5°.

17. The wireform of claim 16, wherein the points of tangency at the opposite ends of any one curvilinear segment are located along the respective curvilinear first and second apices at an external angle of about 70° with respect to the corresponding longitudinal apical axes.

18. An intraluminal graft that is highly compactable, comprising:
a biocompatible pliable tube, and
a plurality of annular wireforms, each wireform defining a central axis and including in a radially expanded state:
a wire having a zig-zag shape with a plurality of first apices extending in one axial direction and a plurality of second apices extending in the opposite axial direction, and a plurality of curvilinear segments extending between and connecting the alternating first and second apices, the curvilinear segments each having a direction of curvature in the same rotational orientation about the central axis as an adjacent curvilinear segment so that in a reduced-diameter state the curvilinear segments nest together.

19. The graft of claim 18, wherein the wireform is formed at least partially of resilient material and biased to said radially expanded state such that said wireform will self-expand to said radially expanded state when at body temperature and unconstrained.

20. The graft of claim 18, wherein said wireform is at least partially formed of malleable material which is initially formed to said reduced-diameter state, and is plastically deformable to said radially expanded state.

21. The graft of claim 18, wherein the first apices are co-planar, and the second apices are co-planar.

22. The graft of claim 18, wherein the first and second apices are curvilinear and have radii of curvature and a corresponding center of radius.

23. The graft of claim 22, wherein each curvilinear segment connects to the adjacent first and second apices at points of tangency along the respective radii of curvature of the first and second apices.

24. The graft of claim 18, wherein the plurality of wireforms are axially spaced apart and affixed to the pliable tube.

25. The graft of claim 18, wherein the wireforms are located substantially within the pliable tube.

26. The graft of claim 18, wherein the wireforms are threaded through apertures provided in the pliable tube.

* * * * *